United States Patent [19]
Patton et al.

[11] Patent Number: 5,469,744
[45] Date of Patent: Nov. 28, 1995

[54] APPARATUS FOR ACOUSTICALLY INSPECTING A WORKPIECE

[75] Inventors: Thadd C. Patton; David K. Hsu, both of Ames, Iowa

[73] Assignee: Iowa State University Research Foundation Inc., Ames, Iowa

[21] Appl. No.: 260,557

[22] Filed: Jun. 16, 1994

[51] Int. Cl.⁶ .......................... G01N 29/28; G01H 11/00
[52] U.S. Cl. ................................ 73/644; 73/661
[58] Field of Search ............... 73/644, 642, 661; 128/660.03, 660.1

[56] References Cited

U.S. PATENT DOCUMENTS

| | | | |
|---|---|---|---|
| 4,563,900 | 1/1986 | Harada | 73/644 |
| 4,566,333 | 1/1986 | Chubachi | 73/644 |
| 4,796,632 | 1/1989 | Boyd | 73/644 |
| 4,813,402 | 3/1989 | Reichenberger | 73/644 |

FOREIGN PATENT DOCUMENTS

| | | | |
|---|---|---|---|
| 420758 | 4/1991 | European Pat. Off. | 73/644 |

OTHER PUBLICATIONS

"A Computerized Ultrasonic Multiple Array Real-Time Inspection System for the Space Shuttle External Tank Liquid Hydrogen Barrel Welds"; R. G. Harrington; Review of Progress in Quantitative Nondestructive Evaluation; 1984; vol. 3, pp. 1433–1439.

"A Novel Acoustic Coupling Device Using Permeable Membrane"; C. F. Buynak et al.; Amer. Society for Nondestructive Testing, Inc.; Jun. 1987; pp. 743–746.

"Fatigue–induced disbonds in adhesive lap splices of aluminum and their ultrasonic detection"; D. K. Hsu et al.; SPIE Proceedings; vol. 2001; Jul. 1993; pp. 2–13.

"Development of Ultrasonic Inspection for Adhesive Bonds in Aging Aircraft"; D. K. Hsu et al.; Materials Evaluation; vol. 51, No. 12; Dec. 1993; pp. 1390–1397.

*Primary Examiner*—Hezron E. Williams
*Assistant Examiner*—Christine K. Oda
*Attorney, Agent, or Firm*—Flehr, Hohbach, Test, Albritton & Herbert

[57] ABSTRACT

An apparatus for acoustically inspecting a workpiece has a tubular member with a membrane sealing an end of the tube to form a first chamber. An acoustic transducer assembly is mounted in the tubular member. An adapter secured to the tubular member is adapted to contact the workpiece and space the membrane from the workpiece and form a second chamber. In operation, the transducer generates an acoustic wave that travels through coupling fluid disposed in the chambers to strike the workpiece. The acoustic wave is reflected from the workpiece, received by the transducer assembly, and a corresponding electrical signal is sent to a processor for evaluation. Additional features include a fluid conduit providing the independent coupling fluid, a spacer that accommodates workpiece surface variations while maintaining acoustic coupling with the workpiece, and a vacuum housing that removes excess coupling fluid from around the inspection apparatus and workpiece mating surface.

12 Claims, 5 Drawing Sheets

APPARATUS FOR ACOUSTICALLY INSPECTING A WORKPIECE

REFERENCE TO GOVERNMENT RIGHTS

The work disclosed herein was supported by a contract between the Iowa State University and the United States Federal Aviation Administration, contract number W-7405-ENG-82. The United States Government may have certain rights in this invention.

FIELD OF THE INVENTION

The present invention relates to an apparatus and method for acoustically inspecting a workpiece.

BACKGROUND OF THE INVENTION

Nondestructive Inspection (NDI) determines the quality of a workpiece without causing damage to the workpiece. One NDI technique uses acoustic waves to inspect a workpiece. This technique directs an incident acoustic wave at a workpiece, senses a reflection from the workpiece and analyzes the reflection to determine the quality of the workpiece. Acoustic inspection is helpful, for example, to determine the integrity of airplane components including the wing, fuselage and empennage by detecting disbonded lap splices, corroded rivet joints and similar structural defects.

A typical apparatus for acoustically inspecting a workpiece includes a pulse generator electrically connected to a transducer assembly which generates a focused acoustic wave. The acoustic wave travels through a transmission medium and focuses onto the workpiece. Acoustic reflections from the workpiece radiate back to the transducer and causes the transducer to generate a corresponding electrical signal. A processor then analyzes the electrical signal to determine the quality of the workpiece.

Ultrasonic NDI, in particular, can improve the inspection spatial resolution and signal to noise ratio by using a focused acoustic beam. This type of NDI requires a good acoustic coupling between the transducer and the workpiece, and is most effective when applied in an immersion mode.

A known inspection apparatus uses water to serve as a coupling fluid between the transducer and the workpiece. This apparatus employs a perforated membrane between the transducer and the workpiece to retain water, reduce spillage, and leak water onto the workpiece to effect an acoustic coupling between the transducer and the workpiece. The amount of water leakage is determined by the perforation density. An example of such an apparatus is described in C. Bunyak, *A Novel Acoustic Coupling Device Using Permeable Membrane,* Materials Evaluation, vol. 45, p. 743 (June 1987).

In an inspection apparatus with a perforated membrane, there is no control over the amount of water leaking through the membrane's perforations. Moreover the membrane does not adequately accommodate workpiece surface variations that affect acoustic coupling with the workpiece.

OBJECTS AND SUMMARY OF THE INVENTION

The present invention provides an apparatus and method for acoustically inspecting a workpiece. For purposes of the specification, the present invention is called a contact adaptive bubbler (CAB). A method of the present invention includes steps for performing the invention.

An object of the present invention is to provide a CAB that can accommodate workpiece surface variations to provide a superior acoustic coupling with the workpiece.

Another object of the present invention is to provide a CAB with a vacuum housing combination that removes excess fluid from around the CAB and workpiece mating surface.

A first embodiment for acoustically inspecting a workpiece comprises a tubular member with a membrane sealing one end of the tube to form a first chamber. The first chamber receives a coupling fluid. An acoustic transducer assembly is mounted in the tubular member, and is acoustically coupled to the coupling fluid disposed in the first chamber. An spacer extends beyond the one end of the tubular member and is adapted to contact the workpiece and space the membrane from the workpiece to form a second chamber which receives an independent coupling fluid.

In operation, the transducer assembly generates a focused acoustic wave that travels through the coupling fluids and membrane to strike the workpiece. The acoustic wave reflects from the workpiece and travels through the coupling fluids and membrane to strike the transducer assembly which generates a corresponding electrical signal that is sent to a processor for evaluation.

The first embodiment can be combined with additional elements that include a fluid conduit providing the independent coupling fluid, a spacer that spaces the membrane from the workpiece while maintaining acoustic coupling with the workpiece, and a vacuum housing that removes excess coupling fluid from around the inspection apparatus and workpiece mating surface.

DETAILED DESCRIPTION OF A PREFERRED EMBODIMENT

The following description is provided for a preferred embodiment. Those skilled in the art will appreciate that various changes and modifications can be made to the preferred embodiment while remaining within the scope of the present invention. For purposes of the specification, the present invention is called a contact adaptive bubbler (CAB).

Figure 1:
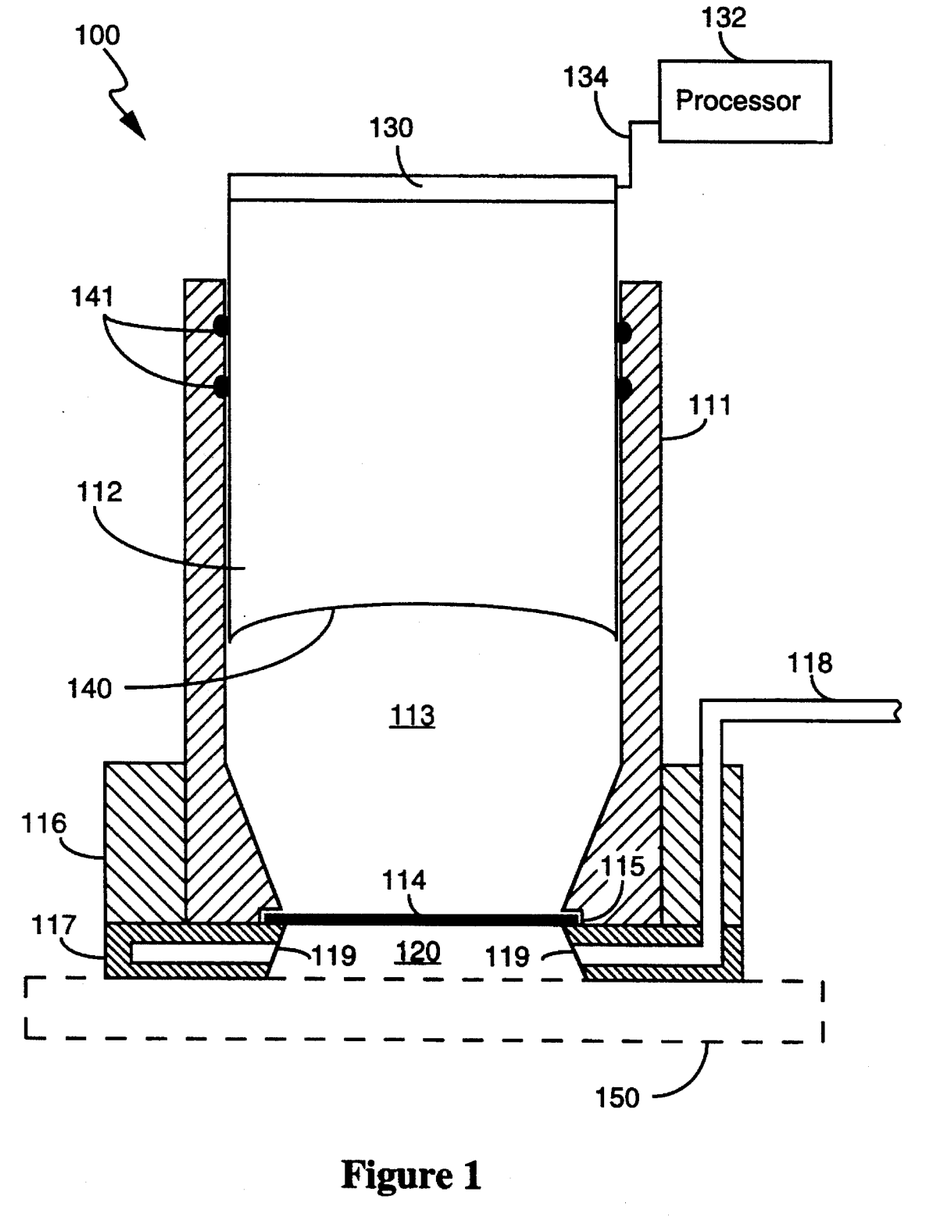
FIG. 1 is a cut-away view of a first embodiment of the present invention.

FIG. 1 shows a cross-section of a CAB 100. An associated transducer assembly includes two parts: a rod 112 partially disposed within tubular member 111, and a piezoelectric transducer 130 connected to a processor 132 via wire 134. Transducer 130 induces acoustic waves in the rod 112 in response to applied electrical pulses. The concave end 140 of the rod 112 focuses the acoustic waves leaving the end 140 onto a workpiece 150. Thereafter, the rod 112 and transducer 130 receive reflected acoustic waves and the transducer 130 generates an output electrical signal in response thereto.

While, the present invention is directed at the CAB, processor 132 is discussed since it is relevant to the operation of the CAB. For purposes of clarification, processor 132 serves two purposes: it generates a signal to drive transducer 130 and induce an incident acoustic wave, and it analyzes a signal received from the transducer generated in response to acoustic waves reflected from the workpiece 150. Any of a number of commercially available processors can be used in the present invention.

Tube 111 provides support for a thin membrane 114 positioned near the end of the tube 111 opposite rod 112. The membrane 114 is suitably supported across the end, as for example, by a press fit between the tube and an annular adapter 117. This is shown in FIG. 1 by providing a seating recess 115. It should be understood that many suitable seals between the tube and the membrane can be used.

The adapter 117 and corresponding collar 116, which are both annular in shape, mate with tube 111. Collar 116 fits over the periphery of tube 111 to be supported by the tube centered over the membrane 114. If necessary, the adapter 117 can be secured to the tube 111 by an O-ring, glue, clamp or other suitable fixative.

As shown in FIG. 1, tube 111 and membrane 114 define a chamber 113, and when combined with rod 112 define an enclosed chamber 113. This chamber is filled with a coupling fluid in contact with all surfaces of the enclosed chamber 113, including the end 140 of the rod 112. O-rings 141 are provided between the tube 111 and rod 112 to effect a fluid tight seal. The rod end 140 surface is parabolic to focus the acoustic waves toward a specific location of the workpiece 150. As such, a specific focal point of the acoustic waves generated by the transducer is at the workpiece surface.

The surface of adapter 117 contacts the workpiece 150. In this context, the adapter 117 is compliant and can be made to conform to the surface structure of the workpiece. For example, if the workpiece is planar, the adapter can have a planar contact surface, and if the workpiece has a curvature, the adapter can have a corresponding curvature.

Adapter 117 and membrane 114 define a second chamber 120, and when combined with the workpiece 150 define a second enclosed chamber 120 in which a second coupling fluid is disposed. The coupling fluid in the second chamber 120 is independent of the coupling fluid in the first chamber, and the second coupling fluid is provided by a conduit 118 through fluid supply holes 119 located on the inner circumference of the adapter 117. The adapter 117 spaces the membrane 114 far enough from the workpiece to accommodate surface variations. In a preferred embodiment, this distance is approximately 1.5 mm.

The coupling fluids are selected to have approximately the same acoustic transmission constants to provide a substantially uniform acoustic impedance between the concave end 140 of the rod 112 and the workpiece 150. Moreover, the membrane is thin to promote the uniformity of the acoustic impedance. A preferred embodiment uses water as the coupling fluids and thin latex, 0.005 mm, as the membrane.

An additional feature of the preferred embodiment is focusing the acoustic beam beyond the membrane to reduce acoustic interference between the immersion transducer's focal spot and the CAB's membrane. This is accomplished by designing the curvature of the concave surface 140 and the length of the tube 111 for a particular set of acoustic parameters.

The CAB is designed to function over a wide range of frequencies including the range of 1 MHz to 15 MHz. For purposes of illustration, a 1 MHz transducer has been constructed having a diameter of 19 mm and a focal length of approximately 25 mm and a 15 MHz transducer has been constructed having a diameter of 12.7 mm and a focal length of 76 mm. It is anticipated that these parameters can be varied with good results.

Figure 2:
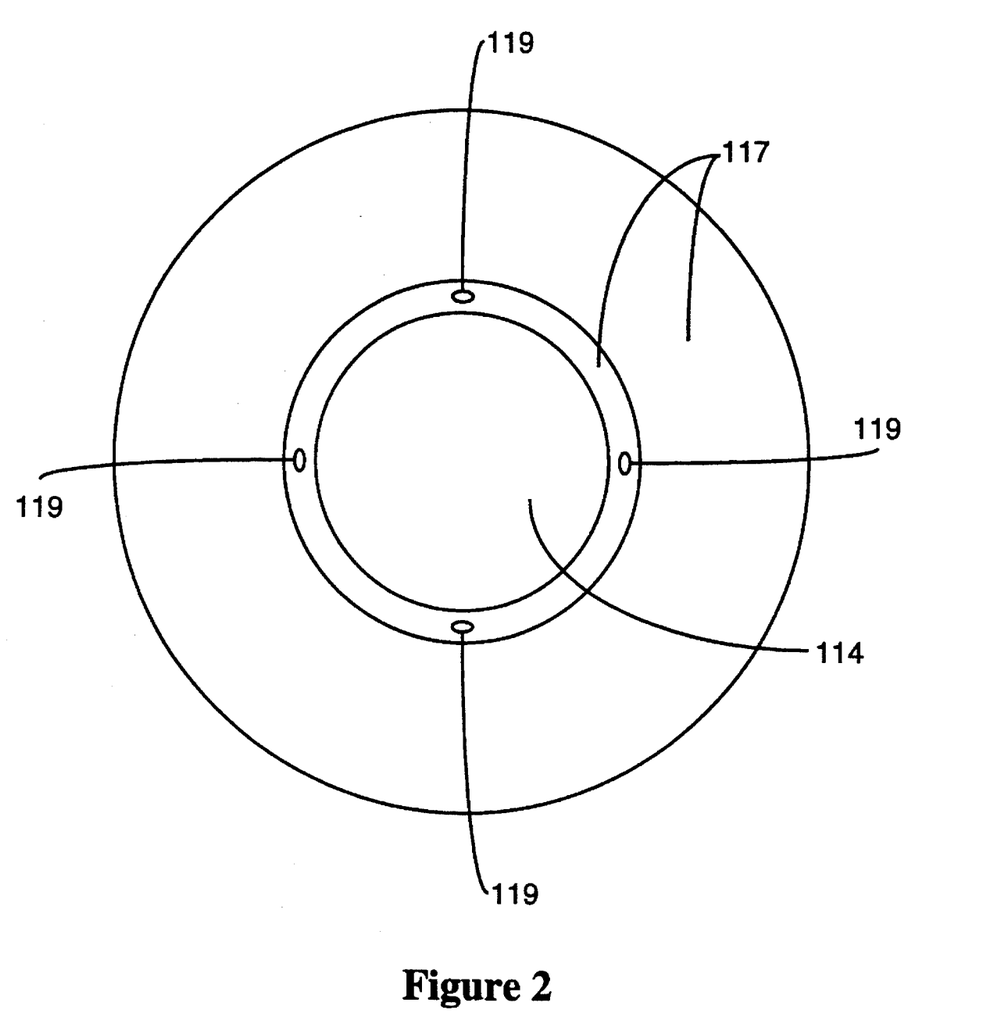
FIG. 2 is a bottom view of FIG. 1.

FIG. 2 shows a bottom view of the CAB 100 including membrane 114, adapter 117, and fluid supply holes 119. This view shows the circular configuration of the preferred embodiment.

As shown in FIG. 2, there are a plurality of fluid supply holes 119 to encourage an even distribution of fluid in chamber 120. In a preferred embodiment, there are four holes 119, but this number can be modified with good results. The coupling fluid is supplied at a rate sufficient to maintain the second chamber 120 full of fluid to promote acoustic coupling with the workpiece 150. This is typically accomplished using a siphon effect, where fluid is replaced into chamber 120 as it leaks from the workpiece contact area. Alternately, a metering valve can be placed in the fluid conduit 118 to control the fluid flow.

In operation, the CAB 100 is placed over a workpiece 150 and fluid is placed in chamber 113 and directed via conduit 118 and fluid supply holes 119 into chamber 120. With coupling fluid in chambers 113 and 120, the transducer rod 112 is effectively coupled to the workpiece 150. Processor 132 generates a finite time signal that is delivered via wire 134 to the piezoelectric transducer 130 which induces acoustic waves in the rod 112. The waves leaving the rod and 140 are focused onto the workpiece 150 through coupling fluids present in the first chamber 113 and second chamber 120.

After striking the workpiece, the acoustic wave reflects back from the workpiece 150, through chamber 120, membrane 114 and chamber 113 to rod 112. The transducer 130 is responsive to the reflected acoustic wave and generates a corresponding second electrical signal that is sent to processor 132 via wire 134. The processor 132 compares the first electrical signal, causing the incident acoustic wave, and the second electrical signal, caused by the reflected acoustic wave to determine the quality of the workpiece.

In many cases where the workpiece is at a height equal to or above the fluid supply, a gravity feed system does not adequately supply fluid and a pump is helpful to provide a pressurized fluid source for the fluid conduit 118. Also, a metering valve can be placed in the conduit 118 for controlling the fluid flow.

Figure 3:
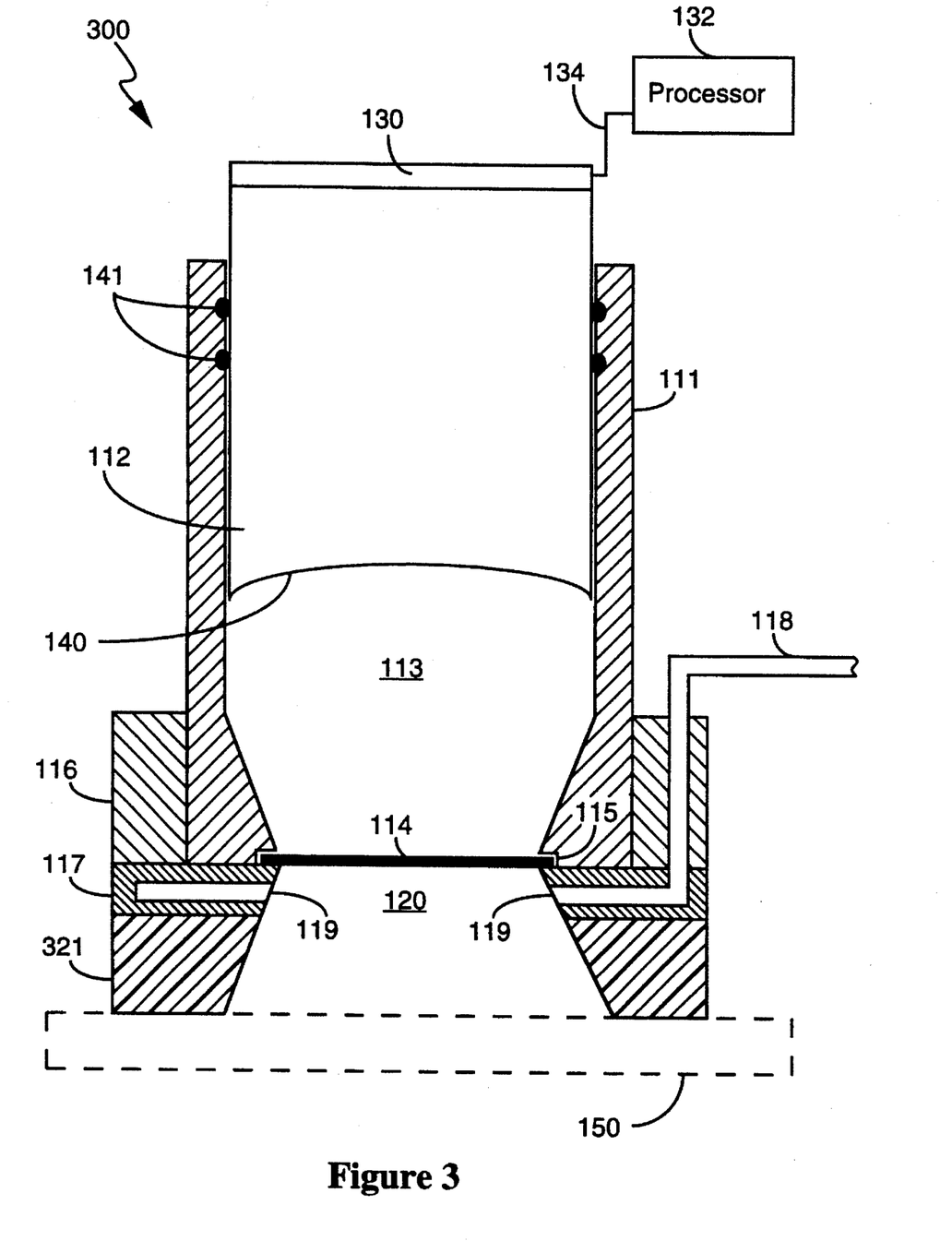
FIG. 3 is a cut-away view of a second embodiment of the present invention.

The first embodiment can be combined with a spacer that enlarges the workpiece contact chamber while maintaining acoustic coupling with the workpiece, effectively increasing the distance between the membrane and workpiece. FIG. 3 depicts CAB 300, which includes spacer 321. The spacer 321 of CAB 300, also called a scanning adapter, fits onto adapter 117. In essence, the spacer is a ring providing an easy glide surface for contact scanning and capturing a pool of fluid in chamber 120 at the exit surface to maintain good acoustic coupling with the workpiece 150.

The spacer 321 creates a sufficient separation between the membrane and the workpiece to overcome surface variations, which include rivets that extend upward from the surface and lap splices joining various layers of materials. Moreover, the spacer 321 includes a compliant material that adapts to surface variations. In a preferred embodiment, the spacer is constructed of flexible low density foam to space the membrane approximately 2–4 mm from the workpiece. The spacer 321 may also have a teflon workpiece contact surface. The spacer 321 can accommodate surface variations including rivets, lap splices and curvatures to form a substantially fluid tight seal and prevent the spillage of coupling fluid. Finally, the spacer 321 can be custom constructed depending on the surface. For example, if the surface is planar, a planar spacer can be constructed, and if the surface contains a curvature, a corresponding spacer can be constructed.

Figure 4:
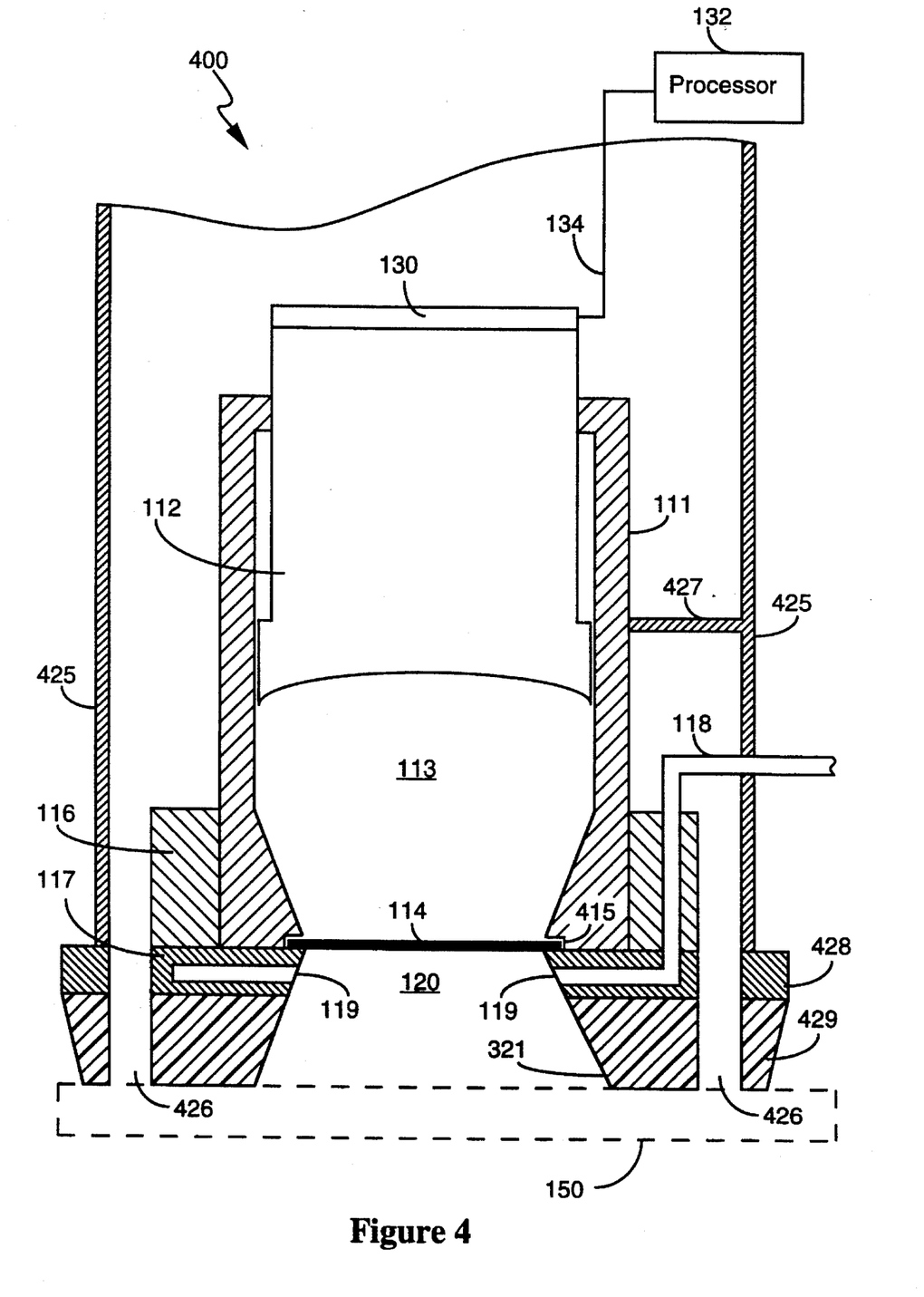
FIG. 4 is a cut-away view of a third embodiment of the present invention.
Figure 5:
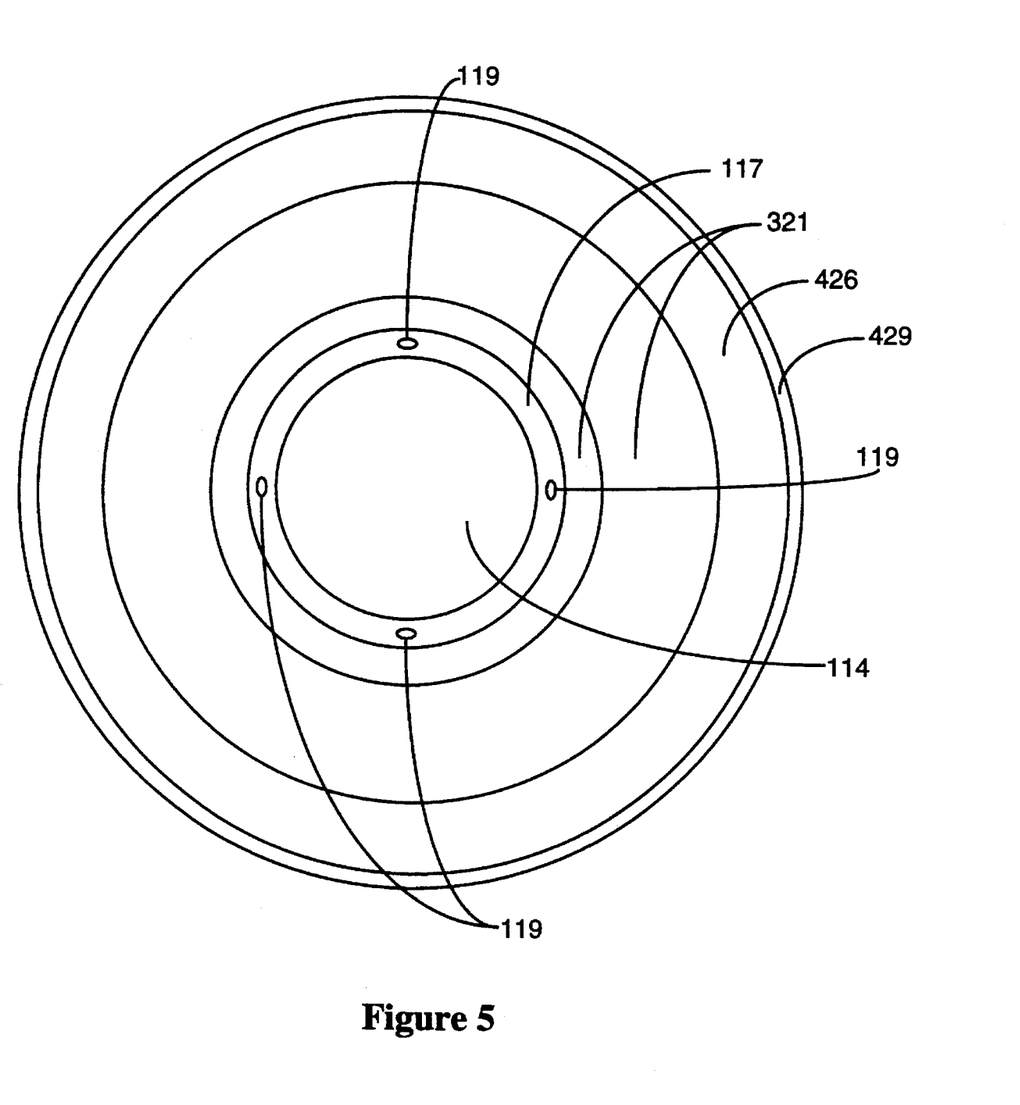
FIG. 5 is a bottom view of FIG. 4.

FIG. 4 depicts a cross-sectional view of a third embodiment of the present invention, CAB 400. CAB 400 includes a water vacuum return system (WVRS) comprising a vacuum housing 425 having vacuum opening 426. The vacuum housing 425 is annular in shape to accommodate the tubular member 111 and is held in place by a plurality of standoffs 427 to position opening 426 at a close proximity to the workpiece mating surface. The vacuum housing 425 also includes an adapter 428 that is similar to adapter 117 and a spacer 429 that is similiar to spacer 321. FIG. 5 is a bottom view of FIG. 4 and shows the circular configuration of the preferred embodiment.

In operation, CAB 400 contains a coupling fluid in chambers 113 and 120 to effect an acoustic coupling between the transducer rod 112 and the workpiece 150. As the CAB 400 is moved over the workpiece surface, some coupling fluid is left behind. This is particularly true where many surface variations exist. The opening 426 is placed peripheral to a workpiece contact member; either the tubular member 111, adapter 117 or spacer 321, depending on the CAB configuration. A vacuum pump (not shown) connected to housing 425 reduces the pressure in housing 425. This causes air to rush in the opening 426, removing excess coupling fluid from the workpiece surface. Since the opening is positioned near the workpiece contact surface and peripheral to the workpiece contact member, the amount of residual coupling fluid left on the workpiece is reduced. Further, if desired, the removed fluid can be reclaimed for future use in the CAB, such as by reintroducing reclaimed water into the conduit 118.

The CAB is ideally suited for applications where ultrasonic NDI using a focused immersion configuration is desired, but due to other constraints, the workpiece can not be immersed in a water bath. With the attachment of the WVRS, the CAB is a water-coupled, self-contained contact inspection system that leaves only a damp area behind when inspection is finished. The CAB can be attached to many commercially available contact scanners and operated on horizontal, vertical, and overhead surfaces.

VARIATIONS ON THE DISCLOSED EMBODIMENTS

Variations to the preferred embodiments include using coupling fluids other than water. Any coupling fluid can be used and the illustration of using water is given because water is readily available and works well. However, there may be applications where it is detrimental to subject a workpiece to water, and for those purposes the preferred embodiment is readily adaptable to use other coupling fluids.

The materials used in the preferred embodiments, including the membrane material, can be varied while remaining within the scope of the present invention.

The spacer 321 can take the place of adapter 117 and provide fluid conduit 118 and fluid supply holes 119.

The preferred embodiments describe a substantially round tube, however, any shape tube can be used including a square or rectangular tube. Also, the transducer rod end need not have a parabolic surface, but could have any surface shape suitable for acoustic NDI.

Having disclosed a preferred embodiment and the best mode, there are a number of modifications that will be obvious to one skilled in the art. This specification is intended to cover all embodiments within the spirit of the invention that is now claimed.

What is claimed is:

1. An apparatus for acoustically inspecting a workpiece, comprising:

a tubular member;

a membrane sealed to one end of said tubular member;

an acoustic transducer assembly including a rod mounted in said tubular member, one end of said rod defining with said tubular member a first chamber and the other end of said rod acoustically coupled to a transducer;

an annular adapter attached to said tubular member, said adapter adapted to contact the workpiece and space said membrane from the workpiece to form a second chamber.

2. The apparatus of claim 1, wherein:

said membrane provides a non-permeable barrier to fluids between said first chamber and said second chamber and allows for acoustic transmission therebetween.

3. The apparatus of claim 1, further comprising:

a conduit to deliver coupling fluid to said second chamber.

4. The apparatus of claim 3, further comprising:

a pump to deliver pressurized fluid to said conduit.

5. The apparatus of claim 1, further comprising:

a vacuum housing having an opening peripheral to said adapter to remove fluid from the workpiece.

6. The apparatus of claim 1, further comprising:

an annular spacer attached to said adapter, said spacer adapted to contact the workpiece and enlarge said second chamber.

7. The apparatus of claim 6, further comprising:

a vacuum housing having an opening peripheral to said adapter to remove fluid from the workpiece.

8. An apparatus for acoustically inspecting a workpiece, comprising:

a tubular member;

a membrane sealed to one end of said tubular member;

an acoustic transducer assembly including a rod mounted in said tubular member, one end of said rod defining with said tubular member a first chamber and the other end of said rod acoustically coupled to a transducer;

an annular adapter attached to said tubular member, said adapter having a conduit to receive coupling fluid, and said adapter adapted to contact the workpiece and space said membrane from the workpiece to form a second chamber.

9. The apparatus of claim 8, further comprising:

a pump to deliver pressurized fluid to said conduit.

10. The apparatus of claim 8, further comprising:

a vacuum housing having an opening peripheral to said adapter to remove fluid from the workpiece.

11. The apparatus of claim 8, further comprising:

an annular spacer attached to said adapter, said spacer adapted to contact the workpiece and enlarge said second chamber.

12. The apparatus of claim 11, further comprising:

a vacuum housing having an opening peripheral to said adapter to remove fluid from the workpiece.

* * * * *

UNITED STATES PATENT AND TRADEMARK OFFICE
CERTIFICATE OF CORRECTION

PATENT NO. : 5,469,744
DATED : November 28, 1995
INVENTOR(S) : Patton et al.

It is certified that error appears in the above-indentified patent and that said Letters Patent is hereby corrected as shown below:

Column 1, line 8, change "Federal Aviation Administration" to --Department of Energy--.

Signed and Sealed this

Ninth Day of April, 1996

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,469,744
DATED : November 28, 1995
INVENTOR(S) : Patton et al.

It is certified that error appears in the above-indentified patent and that said Letters Patent is hereby corrected as shown below:

Column 1, lines 6-10, replace the paragraph with --The work disclosed herein was supported by the United States Federal Aviation Administration under a contract between the Iowa State University and the Department of Energy, contract number W-7405-ENG-82. The United States Government may have certain rights in this invention.--

Signed and Sealed this

Fourth Day of March, 1997

Attest:

BRUCE LEHMAN

*Attesting Officer*     Commissioner of Patents and Trademarks